US009022982B2

(12) United States Patent
Karlsson et al.

(10) Patent No.: US 9,022,982 B2
(45) Date of Patent: *May 5, 2015

(54) INJECTION DEVICE

(75) Inventors: Anders Karlsson, Saltsjö-Boo (SE); Stephan Olson, Danderyd (SE)

(73) Assignee: SHL Group AB, Nacka Strand (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/127,008

(22) PCT Filed: Jun. 7, 2012

(86) PCT No.: PCT/SE2012/050614
§ 371 (c)(1),
(2), (4) Date: Dec. 17, 2013

(87) PCT Pub. No.: WO2012/173553
PCT Pub. Date: Dec. 20, 2012

(65) Prior Publication Data
US 2014/0148763 A1    May 29, 2014

Related U.S. Application Data

(60) Provisional application No. 61/498,541, filed on Jun. 18, 2011.

(30) Foreign Application Priority Data

Jun. 17, 2011    (SE) ........................ 1150553

(51) Int. Cl.
*A61M 5/315*    (2006.01)
*A61M 5/28*    (2006.01)
*A61M 5/32*    (2006.01)
*A61M 5/20*    (2006.01)

(52) U.S. Cl.
CPC ............. *A61M 5/31565* (2013.01); *A61M 5/28* (2013.01); *A61M 5/326* (2013.01); *A61M 5/3204* (2013.01); *A61M 5/2033* (2013.01); *A61M 5/3157* (2013.01); *A61M 5/31583* (2013.01); *A61M 2005/2013* (2013.01); *A61M 2005/206* (2013.01); *A61M 2205/582* (2013.01); *A61M 2205/583* (2013.01)

(58) Field of Classification Search
CPC ................................................. A61M 2005/208
USPC ......... 604/135–137, 193, 198, 212, 214, 218, 604/232, 235, 241
See application file for complete search history.

(56) References Cited

U.S. PATENT DOCUMENTS

2006/0287630 A1    12/2006    Hommann

FOREIGN PATENT DOCUMENTS

| EP | 1728529 A1 | 6/2006 |
|---|---|---|
| WO | 2009/007229 A1 | 1/2009 |
| WO | 2009/037141 A1 | 3/2009 |
| WO | 2009/047247 A1 | 4/2009 |
| WO | 2012/173554 A1 | 12/2012 |

OTHER PUBLICATIONS

Sweden Patent Office, Int'l Search Report in PCT/SE2012/050614, Oct. 2, 2012.
Sweden Patent Office, Written Opinion in PCT/SE2012/050614, Oct. 2, 2012.

*Primary Examiner* — Theodore Stigell
*Assistant Examiner* — Amber Stiles
(74) *Attorney, Agent, or Firm* — Piedmont Intellectual Property

(57) ABSTRACT

The invention relates to an injection device comprising a housing, a container holder arranged within said housing, the container holder being configured for accommodating a medicament container having a needle attached to one end thereof and a stopper sealingly and slidable arranged inside the medicament container at the other end thereof, a plunger rod being arranged with a proximal end thereof contactable with said stopper, a first and a second energy accumulating member arranged in the interior of the housing of the injection device and adapted to accumulate and store energy, plunger drive means being slidable arranged in relation to the plunger rod, being rotationally locked to the plunger rod and being rotatable in relation to the housing, the plunger drive means being operationally associated with the first energy accumulating member, a container driver arranged for being connectable to the container holder and threadedly connected to the plunger rod, the container driver being operationally associated with the second energy accumulating member such that due to an output axial force from the second energy accumulating member, the container holder and the plunger rod are axially moveable in relation to the housing a predetermined distance towards the proximal end of the injection device from an initial locked position to a second position whereby a needle penetration is performed, wherein the plunger drive means are locked from being rotated by the container driver, and wherein the plunger drive means are released such that due to an output torque from said first energy accumulating member, the plunger drive means are allowed to be rotated and the plunger rod is urged towards the proximal end of the injection device whereby an injection is performed.

19 Claims, 14 Drawing Sheets

INJECTION DEVICE

TECHNICAL FIELD

The present invention relates to an injection device having several automatic functions such as automatic penetration, automatic injection and automatic safety means for preventing from accidental needle sticks and in particular an injection device capable of handling medicament in fluid form having high viscosity.

RELATED ART

The present invention relates to injection devices for injecting medicament in fluid form having high viscosity which means that these devices require high forces in order to press the fluid through a needle when injecting the medicament.

Auto-injectors, or pen-injectors have been on the market for many years. One of the first auto-injectors was developed for war-times, which was activated by pressing the injector against a body part for activating it. The main concern was to have the medicament injected as fast as possible, without much concern for the patient or for handling safety aspects. During the recent years some medicaments have been developed such that these have to be injected by the patients themselves. Therefore, depending on the intended use and type of medicament, it has also been developed injection devices having a varying degree of automatic functions to facilitate the injection of medicaments in a reliable and safe way for patients and even for trained personnel; e.g. physicians, nurses.

Auto-injector devices having an automated injection function often comprises a housing, a spirally wound compression spring acting on a plunger rod which in its turn acts on a stopper inside a medicament container for expelling the medicament through an attached needle to the container. Normally, one end of the spring is often abutting an inner end surface of the housing, which means that the housing has to be dimensioned to the force of the spring. When fluids with high viscosity are to be injected using an auto-injector, high forces are required to expel the medicament through a fine needle. Consequently, the spring becomes very large both regarding the diameter of the wound spring and also the diameter of the thread of the wire. The size of the spring means that the device becomes large, and for some applications and customers, such sizes of the devices are not acceptable.

WO 2009/037141 discloses an automatic injection device comprising a housing and a container holder arranged within said housing. The container holder has a container adapted to contain a medicament to be delivered through a needle attached to the container and a stopper sealingly and slidable arranged inside said container. The injection device further comprises a spring means arranged in the interior of the device and adapted to store energy, and plunger drive means comprising a plunger rod driving member connected to said spring means and threadly engaged to a plunger rod which is arranged with a proximal end in contact with said stopper, such that when said plunger rod driving member is rotated due to an output torque from the spring means, the plunger rod is urged towards the proximal end of the device. The injection device further comprises container driver means arranged and designed to be fixedly connected to the container holder and to be releasably connected to the plunger rod, such that when said plunger rod is urged towards the proximal end of the device, the container holder is moved a predetermined distance towards the proximal end of the device whereby a needle penetration is performed and whereupon the continuous movement of said plunger rod forces said container driver means to be released from said plunger rod whereby an injection is performed.

The injection device of WO 2009/037141 uses a single spring means for needle penetration and subsequent medicament injection. However, for high viscous liquids, the spring means has to provide a respective high spring force in order to expel the medicament from the medicament container. Such high spring force can, however, not be used for the preceding needle penetration at the injection site as this would cause discomfort to the user and even damage skin and tissue of the user.

Moreover, using a single spring for needle penetration and medicament injection may increase the overall diameter of the device. The diameter of the injection device primarily depends on the diameter of the spring. The longer plunger movement, the wider is the spring diameter. Using the spring also for needle penetration additionally increases the diameter of the spring and thus of the device.

SUMMARY OF THE INVENTION

In order to overcome one or several of the above-mentioned problems, an injection device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The injection device of the present invention comprises a housing and a container holder arranged within the housing. The container holder is configured for accommodating a medicament container.

The housing may comprises a proximal housing part, a distal housing part, a proximal intermediate housing part, and a distal intermediate housing part. In the assembled state of the injection device, the proximal housing part, the distal housing part, and the distal intermediate housing part may form the outer surface or appearance of the injection device. However, the invention also encompasses configurations where the housing comprises less or additional housing parts. The housing parts may have a generally cylindrical configuration, such as a circular, elliptical, or square, or substantially square cylindrical configuration.

A removable front cap may close the proximal opening of the housing.

In a preferred embodiment, the proximal intermediate housing part is coaxially located inside the proximal housing part and the distal intermediate housing part so that it overlaps with both in order to form a connecting structure for connecting these two with each other. The outer surface of the proximal intermediate housing part and the inner surfaces of the proximal housing part and the distal intermediate housing part, respectively, may thus be provided with mating engagement structures. Such a connecting engagement may be provided by circumferential groove-rib-structures, and may be releasable.

However, it is also encompassed by the invention that the proximal housing part and the distal intermediate housing part are connected by other connecting structures not requiring a proximal intermediate housing part.

The distal intermediate housing part may have an stepped configuration seen in axial direction such that a proximal part thereof forms part of the outer appearance of the injection device, whereas a distal part thereof has a smaller cross sectional area relative to the cross sectional area of the proximal part so that the proximal end of the distal housing part can overlap with this part having a smaller cross sectional area to connect the distal intermediate housing part and the distal housing part with each other. Again, circumferential groove-rib-structures can be provided as connecting mechanism.

However, alternatively, the distal intermediate housing part may have not have a stepped configuration but rather at its distal end the same cross sectional size and shape as the distal housing part. In such case, the distal intermediate housing part and the distal housing part may be connected with other for example by means of a coaxial sleeve located outside or inside these parts and partially overlapping with both.

The medicament container holder is preferably at least with its proximal part located within the proximal housing part. The medicament container holder may comprise one or more container holder guides. Preferably, the container holder guides are longitudinally arranged at opposite outer sides of container holder. The container holder guides are received in corresponding groove structures provided at the inner surface of the proximal housing part so that the medicament container holder is axially movable and guidable in relation to the housing but is locked from being rotated relative to the housing, in particular relative to proximal housing part.

The medicament container is an optional component of the injection device in that it may be insertable into the injection device by the user, for example by replacing an empty medicament container after use of the injection device. Moreover, the injection device is not necessarily delivered in its fully assembled state, i.e. with the medicament container already accommodated in the injection device upon delivery of the injection device.

The medicament container may be a commonly used medicament container having a needle attached to one end thereof and a stopper sealingly and slidable arranged inside said medicament container at the other end thereof.

In a preferred embodiment of the invention, the housing, for example the proximal housing part comprises at least one window. This window may extend axially along a certain length of the housing. In a further preferred embodiment, more than one, for example two such windows are provided. In case of two windows, these may be located at opposite sides of the proximal housing part. Such window allows the user to view the state of the injection, i.e. whether the injection device is still in its initial stage with the medicament not yet being injected, or whether the medicament container is already emptied. Through the window(s), the user can see the medicament container accommodated at least in the proximal housing part. Moreover, in the expelled state, the user may see the plunger rod through the window.

The injection device may further comprises a needle shield sleeve or guard arranged slidable in a proximal part of the housing and being capable of acting on a container driver locking means when said needle shield sleeve is pressed against an injection site. The needle shield sleeve initially covers the needle of the medicament container. Thus, the needle is covered or retracted until the injection device is actuated and may not be unintentionally contacted until this moment. The needle shield sleeve is movable between a proximal and a distal position. The needle shield sleeves is preferably contacted and moved when the injection device is positioned at the injection site. On the other hand, the removable front cap at the proximal opening of the housing prevents the needle shield sleeve from being accidentally moved prior to use of the device.

At its distal end, needle shield sleeve may comprises one or more, preferably two, tongue extensions. In case of two tongue extensions, these may be arranged on opposite sides, relative to the longitudinal center axis of the injection device. The proximal part of needle shield sleeve is preferably of generally cylindrical form (assuming generally cylindrical shape of the medicament container). The most proximal part is a fully closed cylinder from which the two tongue extensions project, and extends from the proximal end of the needle shield sleeve a certain distance towards the distal end of the injection device. In a preferred embodiment, the tongue extensions comprise three areas. A first, most proximal area is formed by two cylinder segments having the same radius/diameter as the closed cylindrical most proximal part of needle shield sleeve. The distal parts or areas of tongue extensions are spaced from each other at a greater distance than the diameter of the cylindrical part. In between of these two areas, an intermediate area is provided that forms a transition between the smaller diameter of the cylindrical area and the greater distance at the distal end of the tongue extensions. In general terms, the needle shield sleeve has a widening configuration in that it widens from the proximal end towards the distal end thereof. Such configuration may as well be provided by tongue extensions being inclined relative to the longitudinal axis, and having a single or two distinct areas only.

The injection device of the present invention may further comprise a container driver locking means that is rotatable in relation to the housing and to a container driver. The container driver locking means may be provided distal to the needle sleeve shield. The container driver locking means is configured to hold the container driver in its initial locked position and to release said container driver from its initial locked position towards the proximal end of the injection device to the second position.

Thus, the container driver locking means provides a mechanism that prevents the container driver (locking mechanism) from being actuated, i.e. from being set in a delivery position, before the device is ready for use. Preferably, this functionality is provided by a configuration of the container driver locking means and the container driver such that actuation of the container driver is prevented before the injection device is in contact with the injection site.

The container driver locking means may be a generally ring-shaped element. The container driver locking means is preferably located proximal to the container driver.

Furthermore, the container driver locking means is rotatable in relation to the housing and in engagement with the needle shield sleeve.

The needle shield sleeve and the container driver locking means are preferably operationally connected such that axial movement of said needle shield sleeve towards the distal end of the injection device causes said container driver locking means to perform a rotational movement. Such rotational movement of the container driver locking means results in a release of said container driver.

Such operational connection may be provided by one ore more groove structures provided at the outer surface of the container driver locking means. Each groove structure preferably has two segments, namely an inclined groove, i.e. a groove being inclined with respect to the longitudinal axis of the device, and a longitudinal axial groove, i.e., extending parallel to the longitudinal axis of the device. In the initial position of the injection device, radial protrusions formed at the inner surface of the tongue extension are located in the inclined groove of the groove structures. When the injection device is placed on an injection site the needle shield sleeve is thereby pushed or moved towards the distal end of the injection device. Such displacement of the needle shield sleeve causes the protrusions to move in or slide along the inclined groove towards the distal end of the container driver locking means. Since the container driver locking means is rotatable in relation to the housing but longitudinally fixed (in that it abuts against the container driver), and the needle shield sleeve is rotationally locked, longitudinal displacement of the needle shield sleeve towards the distal end of the injection device results in a rotational movement of the container driver locking means, allowing the protrusions to slide towards the distal ends of inclined grooves.

The injection device further comprises a container driver that is arranged for being connectable to the container holder and threadedly connected to a plunger rod. The container driver is operationally associated with an energy accumulating member (described in detail below) such that due to an output axial force from said second energy accumulating member, the container holder and the plunger rod are axially moveable in relation to the housing a predetermined distance towards the proximal end of the injection device from an initial locked position to a second position whereby a needle penetration is performed.

At its proximal side, the container driver preferably comprises at least one container driver arm. In a more preferred embodiment, two container driver arms may be present. The container driver arms each comprise an engagement opening being configured for engagement with, for example, corresponding engagement protrusions projecting from container holder tongue extensions provided at the distal end of the container holder. Thus, the medicament container holder is connected with the container driver, and longitudinal displacement of the container driver towards the proximal end of the injection device results in a movement of the medicament holder towards the proximal end of the injection device whereby a needle penetration is performed.

The container driver may comprise at least one rotational locking rib. In a preferred embodiment, more than on, such as three or four rotational locking ribs may be provided. In the assembled state of the injection device, the rotational locking ribs are located or received in corresponding locking grooves arranged on the inner surface of the proximal intermediate housing part. The locking ribs as well as the corresponding grooves preferably extend in longitudinal direction. Such structure prevents the container driver from being rotated itself, i.e. the container driver is movable in longitudinal direction relative to the housing but rotationally locked.

According to a preferred embodiment, the container driver comprises at least one ledge. For example, two ledges are provided. These ledges, for example, are located in a plane being perpendicular to the longitudinal axis of the injection device to form partial circumferential abutments such that with these ledges, the container driver initially abuts against stop ribs located at the inner surface of the container driver locking means. Thus, the container driver at its proximal side is partially overlapped by the container driver locking means. The stop ribs are located proximal to the ledges so that they form a stop against proximal axial movement of the container driver. The stop ribs may have the form of corresponding partial circumferential abutment projections. Thus, in the initial position of the injection device, i.e., prior to its use, the container driver and thus the medicament container holder are prevented from being moved proximally because such movement is blocked by the container driver locking means due to the abutment of the ledges against the stop ribs. Only upon rotational movement of the container driver locking means, the stop ribs are moved out of abutment with the ledges. Thus, the container driver is no longer axially locked/blocked by container driver locking means.

The injection device further comprises at least one plunger rod being arranged with a proximal end thereof contactable with the stopper of the medicament container. The plunger rod comprises a threaded structure as well as at least one longitudinal groove at its outer surface. At the proximal end, plunger rod may comprise a plunger rod tip onto which an optional spinner element is snap fit. Spinner element acts on the stopper in the medicament container. With its threaded structure, the plunger rod is screw thread through a central through bore of the container driver, having a mating threaded structure.

A plunger drive means is slidable arranged in relation to the plunger rod. The plunger drive means is also rotationally locked to the plunger rod and rotatable in relation to the housing. Moreover, the plunger drive means is operationally associated with the another energy accumulating member.

The plunger drive means preferably comprises a plunger driver and a plunger drive locking means. The plunger drive locking means may have a distal part of generally cylindrical configuration and a proximal part being formed by a proximal end radial flange. The proximal flange of the plunger drive locking means may comprise at least one rotational lock element projecting essentially radially. In a preferred embodiment, two or more such lock elements are provided. With these rotational lock elements, the plunger drive locking means is initially rotationally locked to the container driver. In order to provide such rotational locking, the container driver comprises corresponding longitudinal ribs at the inner surface of its distal part. The rotational lock elements initially abut against these ribs. Thus, the container driver at least partially overlaps with the plunger driver locking means being located distally to the container driver. The axial length of these locking ribs of the container driver is adapted to the length the container driver and the medical container holders are displaced/displaceable to perform a needle penetration. In more detail, the axial length of the locking ribs is such that upon full displacement of the medicament container holder towards the injection site, the rotational lock elements are finally freed from engagement with the locking ribs. This means that at this stage the plunger drive locking means is no longer rotationally locked by the container driver. In other words, when performing needle penetration, the container holder is moved longitudinally relative to the plunger drive locking means. The plunger drive locking means is axially locked. Such axial lock is provided by a locking structure at the distal end of the plunger drive locking means which is in engagement with a corresponding structure at a distal end of the distal intermediate housing part.

The plunger driver is rotationally locked to the plunger drive locking means but slidable in axial direction in relation to plunger driver locking means. The plunger driver may comprise two internal longitudinal ribs. These longitudinal ribs interact with longitudinal grooves on the outer surface of a plunger rod. Thus, the plunger rod is rotationally locked to plunger driver but may axially slide along these ribs.

Furthermore, the plunger driver may further comprise a longitudinal slit though its wall. With this longitudinal slit, the plunger driver is connected to the inner end of the energy accumulating member. Thus, a force applied to the plunger driver by the energy accumulating member is transmitted to the plunger rod due to the engagement of internal longitudinal ribs into longitudinal grooves.

On the other hand, the plunger driver may comprise at least one external longitudinal rib. For example, four such ribs are provided spaced at 90° to each other. The external longitudinal ribs are slidably received in longitudinal grooves of the plunger drive locking means. Thus, as long as the plunger drive locking means is prevented from being rotated due to the locking engagement with the container driver, the plunger driver and the plunger rod are prevented from being rotated although the force of the first spring acts on the plunger driver. However, once the plunger drive locking means is free to rotate, the plunger driver and the plunger rod also start to rotate, caused by the first spring. In the initial stage of the injection device, i.e. prior to its use, a proximal part of the plunger rod is received in the central opening of the container driver. The central opening of container driver comprises a threaded structure that engages with the threads of the plunger rod. Thus, the threaded proximal section of the plunger rod is screw threaded in the interior of the container driver. Due to this threaded engagement, rotation of the plunger rod upon use of the injection device results in an axial displacement of the plunger rod towards the proximal end of the injection device. In other words, the plunger rod is rotated by the thread engagement in the direction of the medicament container, and causes the stopper in the medicament container holder and in abutment with spinner to move towards the proximal end of the medicament container holder in order to expel medicament. The torque force of spring will continue to drive the plunger rod towards the proximal end of the injection device pressing the stopper to expel medicament through the needle. The container driver slides over along the plunger rod as the plunger rod continues to move towards the proximal end of the device. The injection is completed when the stopper is at the proximal end of the medicament container.

Thus, the container driver forms a locking mechanism that is configured to substantially inhibit medicament delivery when being in an initial locking position. Preferably, when being in a locking position, the locking mechanism is configured to substantially inhibit movement of the at least one plunger rod relative to other parts of the device. Preferably, the container driver (locking mechanism) is configured to substantially inhibit movement of the plunger rod in a proximal direction when being in a locking position. More preferably, the locking mechanism is configured to substantially inhibit movement of the plunger rod in a proximal direction along the longitudinal axis of the device when being in a locking position.

Preferably, the container driver is configured to allow medicament delivery when being in at least one delivery position, i.e. in a second position. When being in the second position after needle penetration was performed, the container driver preferably is configured to allow medicament delivery by injection. Preferably, when being in a delivery position, the container driver is configured to allow at least a certain movement of at least one plunger rod in proximal direction relative to other parts of the device, along the longitudinal axis of the device.

Moving the plunger rod in the proximal direction preferably leads to at least one medicament being expelled from at least one medicament container. The medicament preferably is in a liquid state and the medicament container preferably is positioned in the medicament container holder.

Furthermore, according to the invention, a first energy accumulating member and a second energy accumulating member are arranged in the interior of the housing of the injection device and are adapted to accumulate and store energy. The first energy accumulating member is used to expel medicament after needle penetration, and is preferably located at the distal end of the injection device, within the distal housing part. The second energy accumulating member is used to axially move the medicament container holder in order to perform a needle penetration prior to injection of the medicament. Thus, needle penetration and medicament delivery are decoupled in that different energy accumulating member are used.

The first energy accumulating member of the injection device may comprise a first end connected to the plunger drive means and a second end connected to the housing, for example the distal housing part. Preferably, the first energy accumulating member is a constant force spring. For example, the first energy accumulating member is a clock spring.

The second energy accumulating member may be arranged between the container driver and a ledge on the inner surface of the housing. The second energy accumulating member may be a coil spring or helical spring arranged coaxially with the longitudinal axis of the injection device. In particular, the distal end of the second energy accumulating member may be in contact with the inner surface of a distal radial wall of the distal intermediate housing part. Alternatively, it may be in contact with a ledge provided at the inside of the distal intermediate housing part, proximal to the distal radial wall of the distal intermediate housing part. The proximal end of the second energy accumulating member, on the other hand, abuts against a distal surface of the container driver.

The injection device may further comprise resilient means for urging the needle shield sleeve or guard towards the proximal end of the injection device when the injection device is removed from the injection site. Thus, the needle shield sleeve preferably covers the needle when the injection device is withdrawn from the injection device.

The injection device may further comprise a locking means for locking the needle shield sleeve against moving towards the distal end of the injection device when the injection device is removed from the injection site. As long as the injection device is pressed on the injection site, the protrusions stay at the distal end of the groove structures. However, when the user removes the injection device from the injection site the needle shield sleeve is urged towards the proximal end of the injection device. During this movement, the projections slide from the inclined groove into the longitudinal groove (which are connected at their dist ends to form a kind of V shape) and slide along the longitudinal grooves. The projections are then locked at the proximal ends of the longitudinal grooves by respective locking structures.

Hence, the needle shield sleeve according to the invention is movable or displaceable. More preferably, after the device has been used, the needle shield sleeve is moved and locked in a distal position when the device is withdrawn from the dose delivery site. The needle shield sleeve preferably is urged in a proximal direction by the force of at least one spring. The spring(s) may be provided in the distal are of the needle shield sleeve. Thus, the needle shield sleeve is a protection element, such as a needle protection element or needle protection sleeve that protects the user against inadvertently or accidentally getting in contact with the needle which may be contaminated.

Such needle sleeve proximal displacement may be provided by a proximal housing spring retainer which may generally ring-shaped or substantially ring-shaped, and coaxially arranged with the proximal housing part. The proximal housing spring retainer may surround a distal area of medicament container holder, seen radially between a distal area of medicament container holder and the distal areas of tongue extensions. The retainer may comprises one or more pins that carry springs to push the needle sleeve towards the proximal end of the injection device when the injection device is removed from the injection site after medicament delivery has been performed in order to cover the needle.

Thus, the needle shield sleeve locking means is preferably formed by the container driver locking means. The operational connection between the needle shield sleeve and the container driver locking means may be formed by a cam-groove-mechanism.

The injection device may further comprise an injection indication mechanism for indicating to the user the progress of the injection. The signal may be a visible or tactile signal.

The injection indication mechanism may be an axial injection indication mechanism for indicating to the user that the medicament injection has come to an end. Such axial injection indication mechanism may comprise a signalling element and a drive mechanism for axially driving said signalling member. The drive mechanism is preferably coupled to the plunger drive means. The axial injection indication mechanism may be arranged such that a visible and tactile signal signals to the user end of injection.

According to one embodiment of the invention, an indicator assembly for indicating end of dose comprises indicator, and a U-bracket arranged between the plunger rod and the plunger driver. The U-bracket is connected to the plunger drive locking means such that when the plunger rod is proximally advanced and not in contact with the U-bracket, the U-bracket and the plunger driver are forced distally. The assembly furthermore comprises an indicator rod, being also part of the indicator assembly. A spiral spring is coaxially arranged on the indicator rod, wherein the spiral spring is arranged within the plunger rod. Thus, the indicator rod with the spring is received within a central axial through hole in the plunger rod, whereas the U-bracket lies with its two legs in the two opposing longitudinal grooves of the plunger rod.

When the plunger rod is fully rotated towards the proximal end of injection device, the two legs of the U-bracket are no longer supported by the longitudinal grooves of the plunger rod. Thus, the radial legs at the proximal ends of the U-bracket can disengage the slits in the plunger driver. The spiral spring coaxially arranged with the indicator rod causes indicator assembly to move distally until the indicator contacts the distal front surface of the distal housing part. This causes the distal protrusion of the indicator to project through the indicator opening provided in the centre of the distal wall of the distal housing part. This provides a visible and tactile indication to the user that the complete dose has been expelled.

The injection device of the invention is particularly advantageous for high viscous liquids having a viscosity of approximately 50 cP. For such liquids, the first energy accumulating member preferably gives a plunger force of 70 N in average (i.e. a low load force of 60 N and a high load force of 80 N).

BRIEF DESCRIPTION OF THE DRAWINGS

The following Figures below disclose an embodiment of the invention for illustrational purposes only. In particular, the disclosure within the Figures is not meant to limit the range of protection of the invention. The embodiment shown may be modified in many ways within the scope of the claims.

DETAILED DESCRIPTION OF THE DRAWINGS

Figure 1:
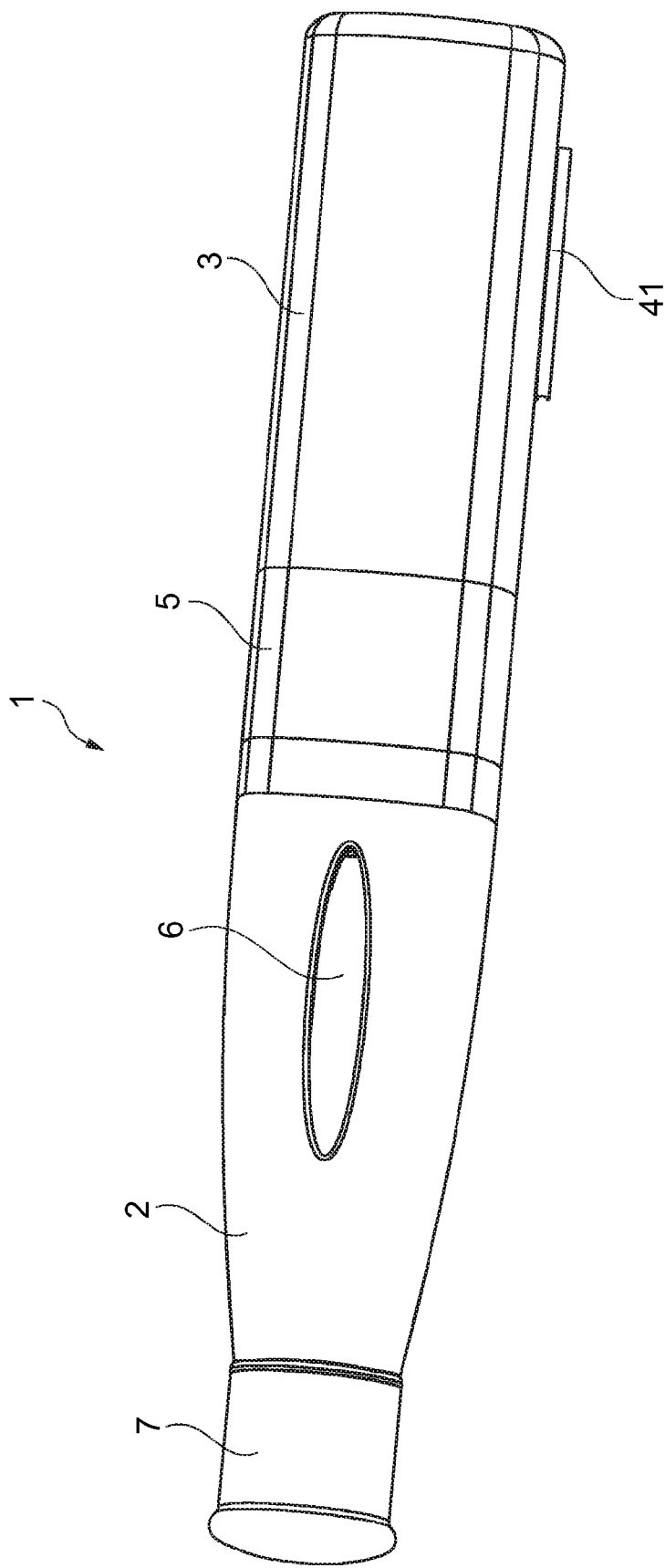
FIG. 1 shows a perspective view of an injection device according to a first preferred embodiment of the invention.

FIG. 1 shows a perspective view of an injection device according to a first preferred embodiment of the present invention. The injection device 1 has a housing that comprises a proximal housing part 2, a distal housing part 3, a proximal intermediate housing part 4 (not shown in FIG. 1), and a distal intermediate housing part 5. In the assembled state of the injection device 1, the proximal housing part 2, the distal housing part 3, and the distal intermediate housing part 5 form the outer surface or appearance of the injection device 1.

As shown in FIG. 1, the proximal housing part 2 comprises at least one window 6. In a preferred embodiment, two such windows are provided located at opposite sides of the proximal housing part 2. Such window allows the user to view the state of the injection, i.e. whether the injection device 1 is still in its initial stage with the medicament not yet being injected, or whether the medicament container is already emptied. Through window 6, the user can see the medicament container accommodated at least in the proximal housing part 2.

Furthermore, FIG. 1 shows front cap 7 which closes the proximal opening of the proximal housing part 2 until the injection device 1 is used.

In FIG. 1, the outer end 41 of a spring can also be seen. This will be described in more detail below.

Figure 2:
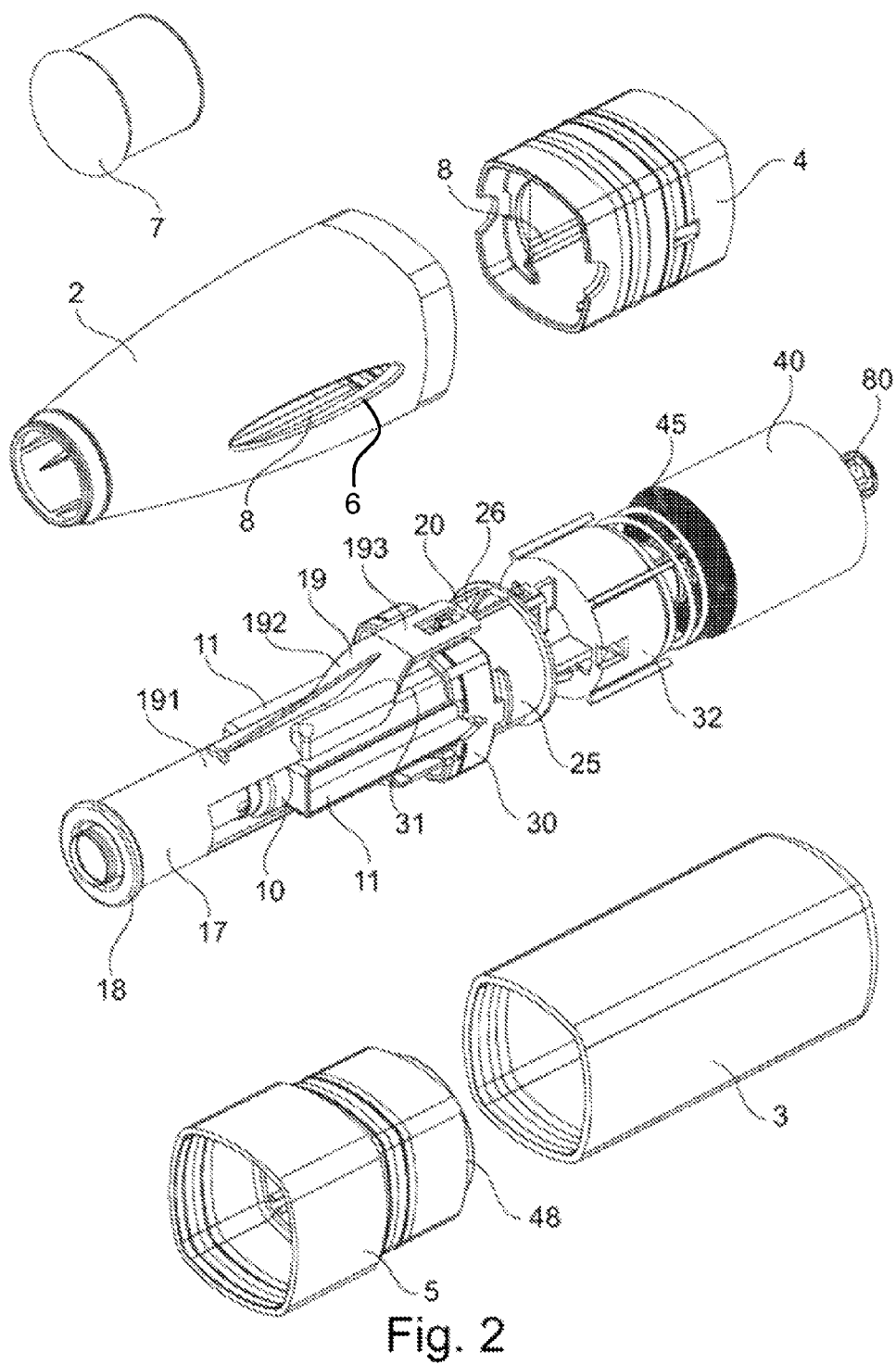
FIG. 2 shows a first exploded view of the injection device according to the first preferred embodiment of FIG. 1.

FIG. 2 shows a first exploded view of the injection device 1 according to the first preferred embodiment of the present invention. In this exploded view of FIG. 2, the proximal housing part 2, the distal intermediate housing part 5 and the distal housing part 3, as well as the front cap 7 are shown "removed" from the injection device 1. Furthermore, FIG. 2 shows proximal intermediate housing part 4. Proximal intermediate housing part 4 forms part of the housing of the injection device 1 but is in fact located in the interior (as clearly shown in the cross-sectional view of FIG. 7) in order to connect the proximal housing part 2 and the distal intermediate housing part 5 with each other. To this end, the outer surface of the proximal intermediate housing part 4 and the inner surfaces of the proximal housing part 2 and the distal intermediate housing part 5, respectively, are provided with corresponding engagement structures such as circumferential groove-rib-structures, a shown in FIG. 2. Thus, the proximal housing part 2 and the distal intermediate housing part 5 can easily be snapped onto the proximal intermediate housing part 4 so that the proximal housing part 2 and the distal intermediate housing part 5 do not fall off of each other. However, the connection between these parts may be releasable so that a medicament container can be inserted into or removed from the proximal part of the injection device 1.

As further shown in FIG. 2, the injection device according to the first embodiment of the invention comprises a medicament container holder 10. In the fully assembled state of the injection device 1, the medicament container holder 10 is at least with its proximal part located within the proximal housing part 2. This will be described in more detail below with reference to FIG. 7. In the preferred embodiment shown in FIG. 2, the medicament container holder 10 comprises a first and a second container holder guide 11. Preferably, the container holder guides 11 are arranged at opposite sides of container holder 10, and extend in longitudinal direction thereof. The container holder guides 11 are received in corresponding groove structures provided at the inner surface of the proximal housing part 2 so that the medicament container holder 10 is axially movable in relation to the housing but is locked from being rotated relative to the housing, in particular relative to proximal housing part 2.

FIG. 2 also shows needle shield sleeve 17 having at its proximal end a needle shield sleeve extension 18. At its distal end, needle shield sleeve 17 comprises two tongue extensions 19 which are arranged on opposite sites, relative to the longitudinal center axis of the injection device 1. The proximal part of needle shield sleeve 17 is of generally cylindrical form. The most proximal part is a fully closed cylinder from which the two tongue extensions 19 project and extend towards the distal end of the injection device 1. In the preferred embodiment shown in the drawings, the tongue extensions 19 basically comprise three areas. The first, most proximal area 191 is formed by two cylinder segments having the same radius/diameter as the closed cylindrical most proximal part of needle shield sleeve 17. The distal parts or areas 193 of tongue extensions 19 are spaced from each other at a greater distance than the diameter of the cylindrical part. In between of these two areas, an intermediate area 192 is provided that forms a transition between the smaller diameter of the cylindrical area 191 and the greater distance at the distal end 193 of the tongue extensions 19. In general terms, the needle shield sleeve 17 has a widened configuration in that it widens from the proximal end towards the distal end thereof.

FIG. 2 further shows proximal housing spring retainer 30 which is generally ring-shaped or substantially ring-shaped, and coaxially arranged with the proximal housing part 2. The proximal housing spring retainer 30 surrounds a distal area of medicament container holder 10, i.e. is located as shown in FIG. 2, radially between a distal area of medicament container holder 10 and the distal areas 193 of tongue extensions 19. As shown in more detail in FIG. 4, the proximal housing spring retainer 30 comprises two pins 31 that carry springs (not shown In FIG. 2) to push the needle sleeve 17 towards the proximal end of the injection device 1 when the injection device 1 is removed from the injection site after medicament delivery has been performed in order to cover the needle 13.

FIG. 2 also shows container driver locking means 25 being a generally ring-shaped element. Container driver locking means 25 is rotatable in relation to the housing and in engagement with the needle shield sleeve 17. This engagement is described in more detail below with reference to FIGS. 3 and 4.

Distal from container driver locking means 25, container driver 32 is located. Container driver 32 is arranged for being connectable to the container holder 10, which will be described in further detail below.

Furthermore, FIG. 2 shows a first energy accumulating member, i.e. first spring 40 which is used to perform an injection, and a second energy accumulating member, for example second spring 45 which is used to axially move the medicament container holder 10 in order to perform a needle penetration prior to injection of the medicament.

Finally, FIG. 2 shows indicator 80 for indicating end of dose.

Further parts shown in FIG. 2 not yet discussed will be discussed in detail below.

Figure 3:
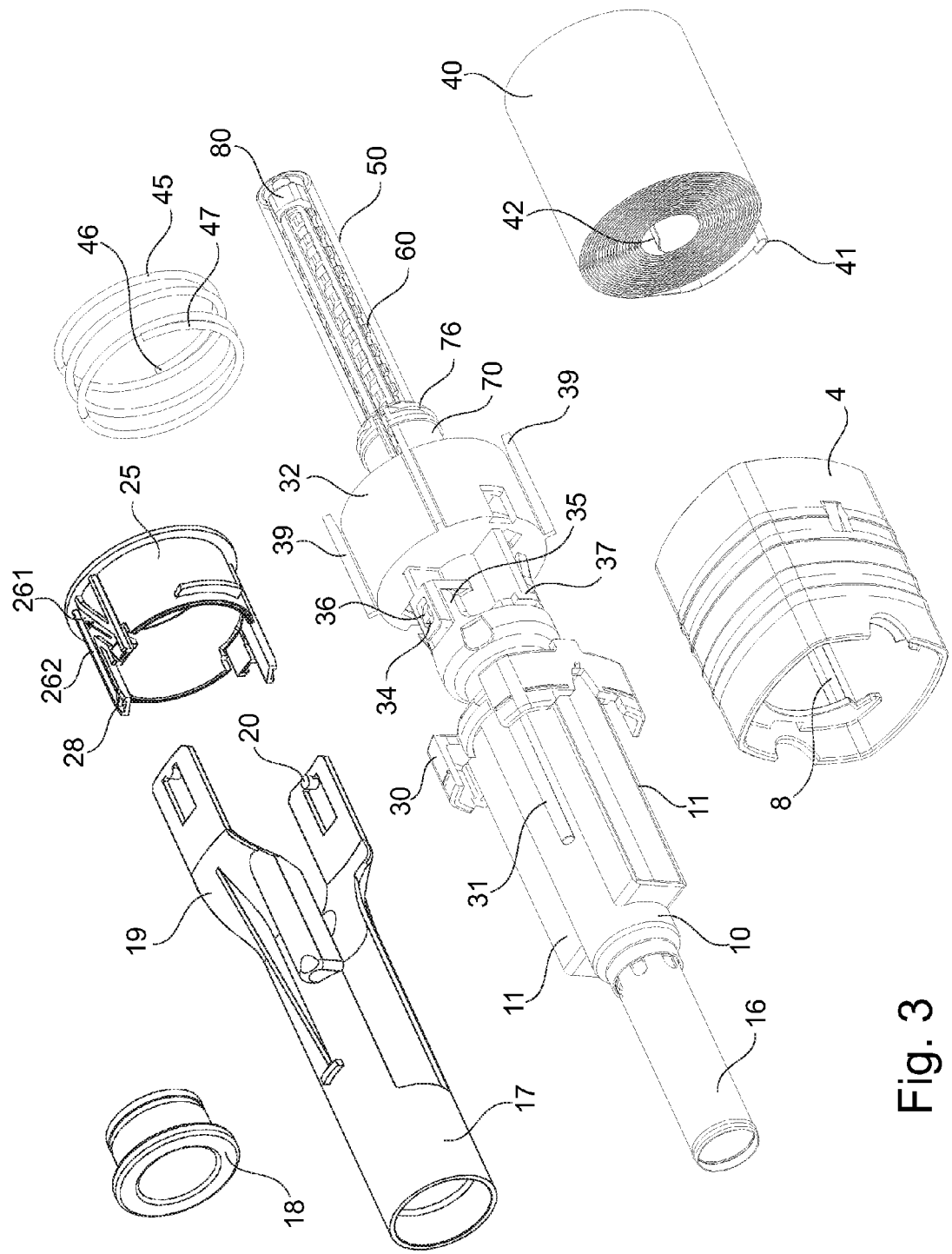
FIG. 3 shows a further exploded view of the injection device according to the first preferred embodiment of the invention.

FIG. 3 shows a further exploded view of the injection device 1 according to the preferred embodiment of the present invention.

In FIG. 3, the needle shield sleeve 17, the needle shield sleeve extension 18, and the container driver locking means 25 are shown "removed" from the injection device assembly. Furthermore, the proximal intermediate housing part 4 and the first spring 40 are shown as individual components in more detail.

In FIG. 3, one of two opposing groove structures 26 of the container driver locking means 25 is shown in more detail. Each groove structure 26 has two segments, namely an inclined groove 261 and a longitudinal groove 262. In the initial position of injection device 1, radial protrusions 20 formed at the inner surface of the distal areas 193 of the tongue extension 19 are located in the inclined groove 261 of the groove structures 26. When the injection device 1 is placed on an injection site, for example the skin of a user, the needle shield sleeve 17 is thereby pushed or moved towards the distal end of the injection device 1. Such displacement of the needle shield sleeve 17 causes the protrusions 20 to move in the inclined grooves 261 towards the distal end of the container driver locking means 25 (which is shown by an arrow and drawn in the inclined groove 261 in FIG. 3). Since the container driver locking means 25 is rotatable in relation to the housing but longitudinally fixed (in that it abuts against the container driver 32), and the needle shield sleeve is rotationally locked, longitudinal displacement of the needle shield sleeve 17 towards the distal end of the injection device 1 results in a rotational movement of the container driver locking means 25, allowing the protrusions 20 to slide towards the distal ends of inclined grooves 261.

As long as the injection device is pressed on the injection site, i.e. as long as the needle shield sleeve 17 is held in its distal position, the protrusions 20 stay at the distal end of the groove structures 26. However, when the user removes the injection device 1 from the injection site, for example after medicament delivery, the needle shield sleeve 17 is urged towards the proximal end of the injection device 1, as described above. During this movement, the projections 20 slide along longitudinal grooves 262 and are locked at the proximal ends of the longitudinal grooves 262 by respective locking structures 28. This prevents that the needle shield sleeve 17 can again be moved towards the distal end of the injection device 1.

FIG. 3 further shows in more detail the medicament container holder 10 with its two container holder guides 11. Furthermore, one of the two pins 31 of the proximal housing spring retainer 30 extending parallel to the longitudinal axis towards the proximal end of the injection device is shown with its full length.

FIG. 3 also shows rigid needle shield remover 16. The rigid needle shield remover 16 comprises at its proximal end an engagement structure, such as a circumferential rib at its outer surface, which is in engagement with a corresponding engagement structure at the inner surface of the front cap 7, for example a corresponding groove (shown in FIG. 7). Due to such engagement, upon removal of the front cap 7, the rigid needle shield remover 16 is withdrawn from the medicament container 12. Furthermore, upon removal of the rigid needle shield remover 16, the rigid needle shield comprising a soft part 14 and a rigid part 15 (see FIG. 5) are also removed from the medicament container 12 due to respective engagement structures engaging the two parts of the rigid needle shield and the rigid needle shield remover 16 with each other.

FIG. 3 also shows in more detail the container driver 32. The container driver 32 comprises at least one rotational locking rib 39. In the preferred embodiment, four rotational locking ribs 39 are provided, three of which are shown in FIG. 3. In the assembled state of the injection device 1, the rotational locking ribs 39 are located or received in corresponding locking grooves 8 arranged on the inner surface of the proximal intermediate housing part 4. The locking ribs as well as the corresponding grooves extend in longitudinal direction. Such structure prevents the container driver 32 from being rotated, i.e. the container driver 32 is movable in longitudinal direction relative to the housing but rotationally locked.

At its proximal side, the container driver 32 comprises at least one container driver arm 33. In the preferred embodiment shown in the drawings, two container driver arms 33 are arranged (see FIG. 4). The container driver arms 33 each comprise an engagement opening 34 being configured for engagement with corresponding engagement protrusions 36 projecting from container holder tongue extensions 35 provided at the distal end of the container holder 10. Thus, the medicament container holder 10 is connected with the container driver 32, and longitudinal displacement of the container driver 32 towards the proximal end of the injection device 1 (by second spring 45) results in a movement of the medicament holder 10 towards the proximal end of the injection device 1 whereby a needle penetration is performed.

Figure 6:
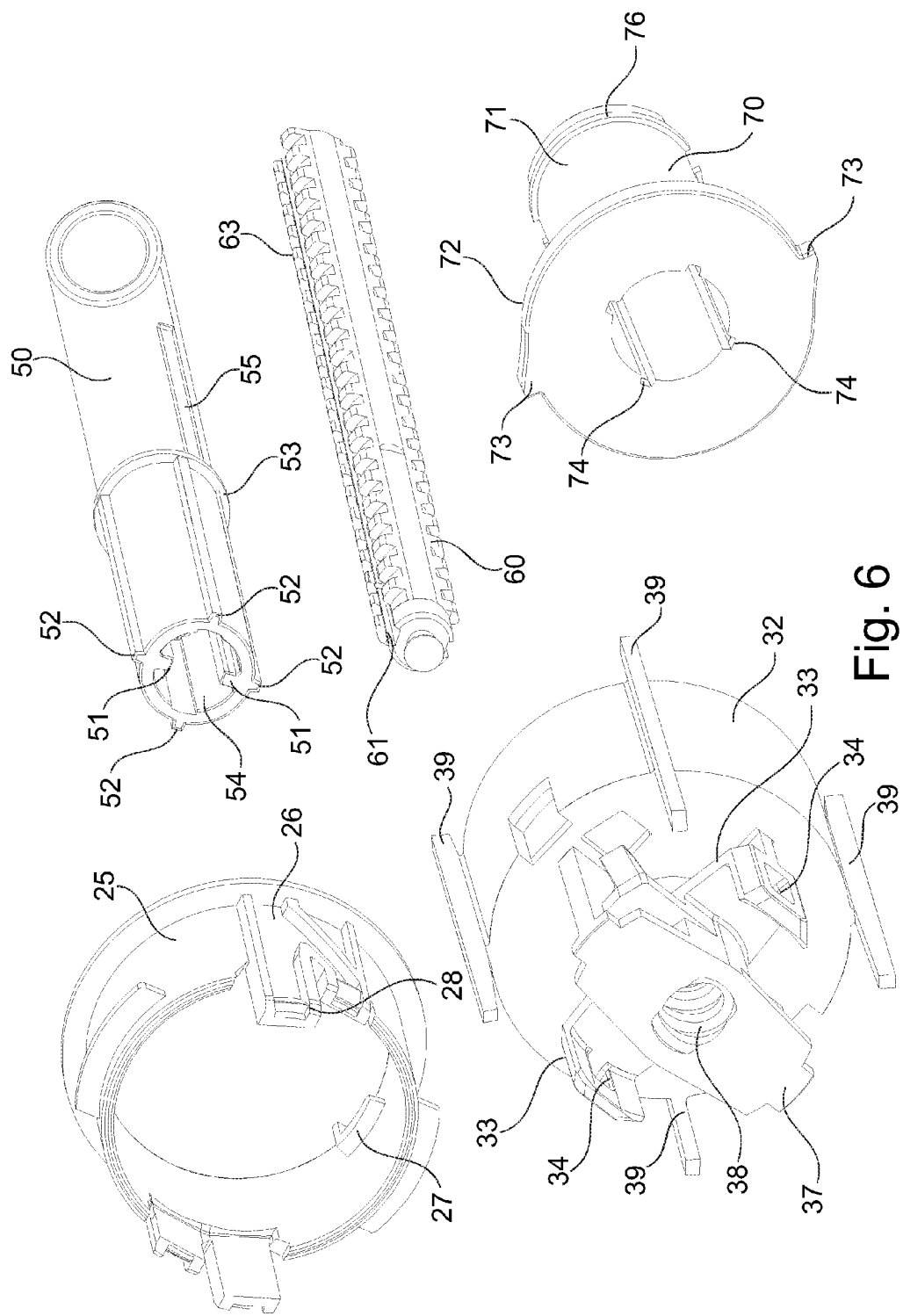
FIG. 6 shows further components of the injection device according to the preferred embodiment.

As can also be seen in FIG. 3, the container driver 32 comprises at least one ledge 37. In the preferred embodiment, two ledges 37 are provided (as can be seen in more detail in FIG. 4). With these ledges 37, the container driver 32 initially abuts against stop ribs 27 located at the inner surface of the container driver locking means 25 (the stop ribs 27 are shown in FIG. 6). Thus, in the initial position of the injection device, i.e., prior to its use, the container driver 32 and thus the medicament container holder 10 are prevented from being moved proximally because such movement is blocked by the container driver locking means 25 due to the abutment of the ledges 37 against the stop ribs 27. Only upon rotational movement of the container driver locking means 25 (caused by distal displacement of the needle shield sleeve 17), the stop ribs 27 are moved out of abutment with the ledges 37. Thus, the container driver is no longer axially locked/blocked by container driver locking means 25.

FIG. 3 also shows plunger driver 50, plunger rod 60, and plunger drive locking means 70. These components are described in more detail below.

Finally, as shown in FIG. 3, first spring 40 comprises an outer end 41 which connects the first spring 40 to the housing, i.e. to the distal housing part 3, and an inner end 42 which connects the first spring 40 to the plunger driver 50. The outer end 41 may, for example, extend through a longitudinal slit in the distal housing part so that it may be engaged with the wall in the form of a hook. The first end 41 can then be seen at the outside, as shown in FIG. 1. Alternatively, the first end of spring 40 is engaged to a mating engagement structure provided at the inner surface of distal housing part 3.

Figure 4:
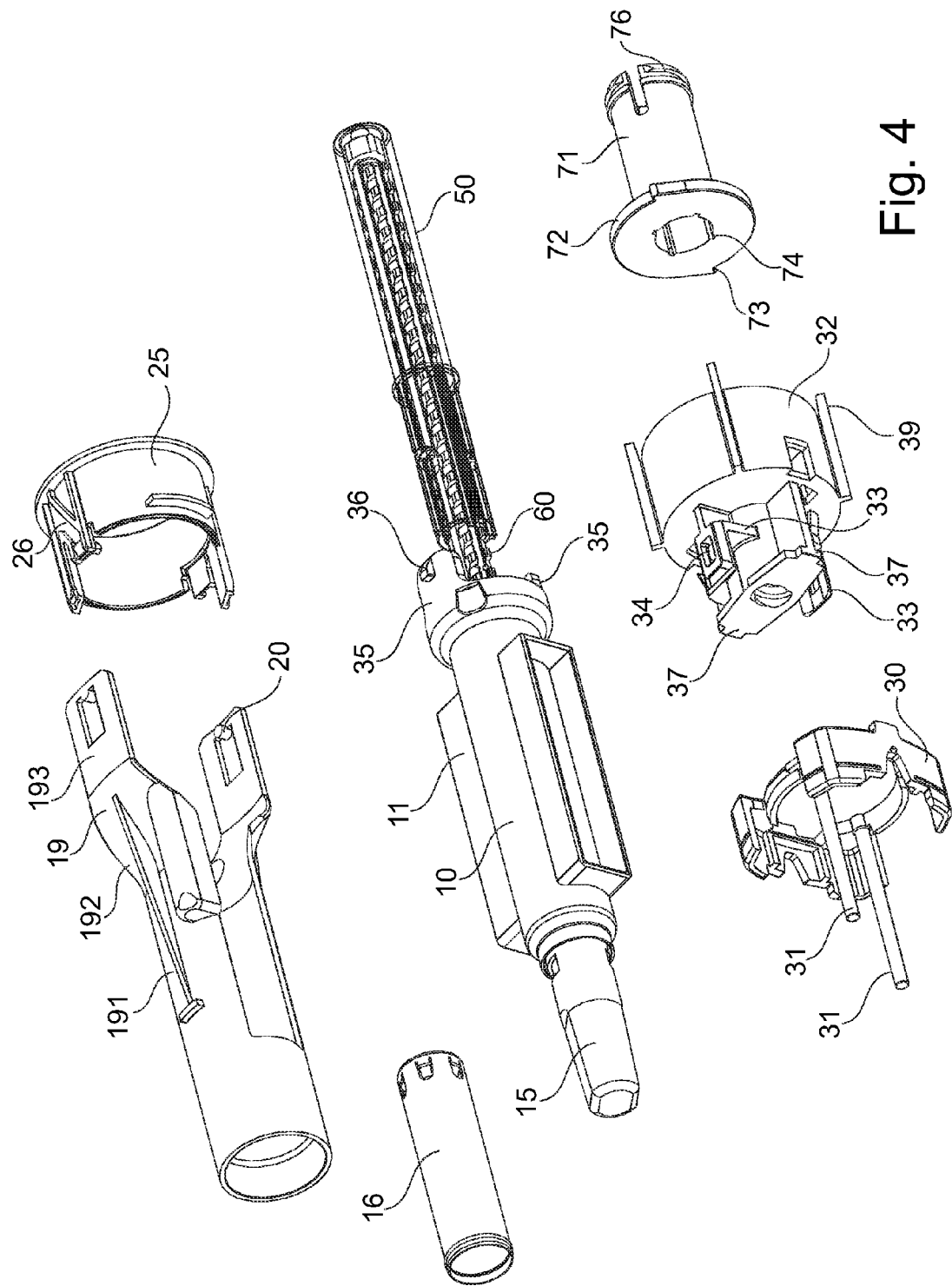
FIG. 4 shows a further exploded view of the injection device according to the first preferred embodiment of the invention.

In the exploded view of FIG. 4, the injection device 1 of the preferred embodiment of the invention is further disassembled. In this drawing, the proximal housing spring retainer 30, the container driver 32, and the plunger drive locking means 70 are shown "removed" from the assembly. In FIG. 4, the distal end of the medicament container holder 10 is shown uncovered by the container driver 32. Thus, the two container holder tongue extensions 35 each having an engagement protrusion 36 can easily be seen.

Furthermore, the two opposing arms 33 of the container driver 32 are shown. In the preferred embodiment, each arm comprises two portions, a first portion extending radially, and a second portion extending in longitudinal direction towards the proximal end of the injection device. Although in the preferred embodiment only two container driver arms 33 and only two corresponding container holder tongue extensions 35 are shown, the invention encompasses other configurations, such as just a single arm-protrusion-pair, or a larger number of arm-protrusion-pairs, such as three or four, for example. Similarly, the container driver 32 may have just a single rotational locking rib 39 but the invention also encompasses container drivers having two, three, five, or six, or even more rotational locking ribs. Furthermore, although the container driver 32 shown in FIG. 4 comprises two ledges 37 for abutment with the container driver locking means 25 only, other configurations having just one or three, four, or more ledges are also encompassed by the invention.

FIG. 4 further shows plunger drive locking means 70. Plunger drive locking means 70 is of generally cylindrical configuration (distal part 71) and comprises at its proximal end radial flange 72. The proximal flange 72 of the plunger drive locking means 70 comprises at least one rotational lock element 73 projecting essentially radially. In the embodiment shown in the Figs, two such lock elements 73 are provided. With these rotational lock elements 73, the plunger drive locking means 70 is initially rotationally locked to the container driver 32. In order to provide such rotational locking, the container driver 32 comprises corresponding longitudinal ribs 75 at the inner surface of its distal part (shown in FIG. 7). The rotational lock elements 73 initially abut against these ribs 75. The axial length of these locking ribs 75 of the container driver 32 is adapted to the length the container driver 32 and the medical container holders 10 are displaced/displaceable to perform a needle penetration. In more detail, the axial length of the locking ribs 75 is such that upon full displacement of the medicament container holder towards the injection site, the rotational lock elements 73 are finally freed from engagement with the locking ribs 75. This means that at this stage the plunger drive locking means 70 is no longer rotationally locked by the container driver 32. In other words, when performing needle penetration, the container holder 32 is moved longitudinally relative to the plunger drive locking means 70. The plunger drive locking means 70 is axially locked. Such axial lock is provided by a locking structure 76 at the distal end of the plunger drive locking means 70 which is in engagement with a corresponding structure at a distal end of the distal intermediate housing part 5 (see FIG. 7).

Figure 5:
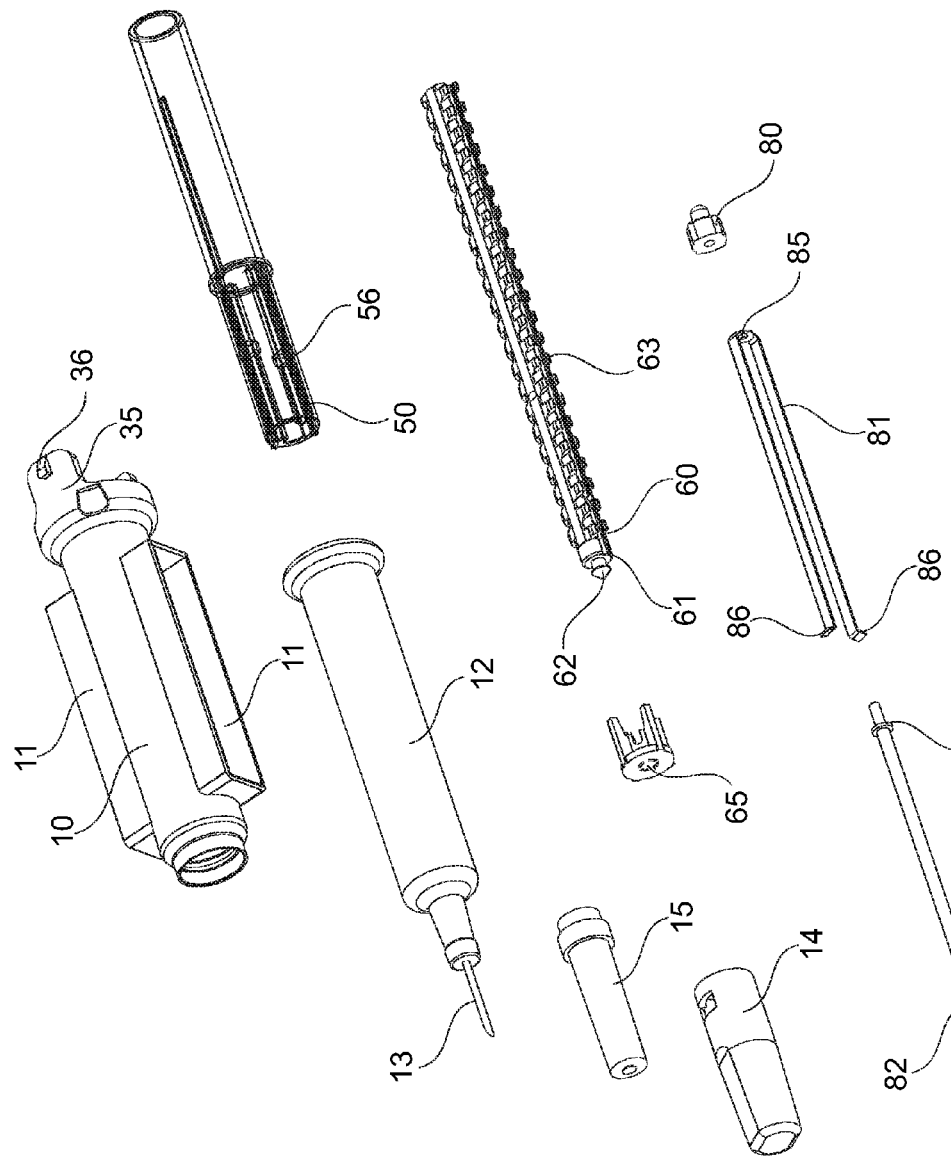
FIG. 5 shows further components of the injection device according to the preferred embodiment.

FIG. 5 shows further components of the injection device 1 according to the preferred embodiment.

As mentioned above, needle 13 of medicament container 12 is covered by a rigid needle shield consisting of a soft part 14 and a rigid part 15.

FIG. 5 further shows plunger driver 50 which is rotationally locked to the plunger drive locking means 70 but slidable in axial direction in relation to plunger drive locking means 70. This will be described in more detail in the context of FIG. 6.

Plunger rod 60 shown in FIG. 5 comprises a threaded structure 63 as well as at least one longitudinal groove 61. At the proximal end, plunger rod 60 comprises a plunger rod tip 62 onto which a spinner element 65 is snap fit. Spinner element 65 acts on the stopper in the medicament container 12.

Finally, FIG. 5 shows an indicator assembly for indicating end of dose, comprising am indicator 80, and a U-bracket 81 arranged between the plunger rod 60 and the plunger driver 50. The U-bracket 81 is connected to the plunger drive locking means 70 such that when the plunger rod 60 is proximally advanced and not in contact with the U-bracket, the U-bracket, the indicator 80 and the indicator rod 82 are forced distally. FIG. 5 also shows indicator rod 82, being also part of the indicator assembly. A spiral spring (not shown in FIG. 5) is coaxially arranged on the indicator rod 82, wherein the spiral spring is arranged within the plunger rod 60. Thus, the indicator rod 82 with the spring is received within a central axial through hole in the plunger rod 60, whereas U-bracket 81 lay with its two legs on the two opposing longitudinal grooves 90 degrees to the two opposing longitudinal grooves 61 of the plunger rod 60.

FIG. 6 shows plunger driver 50. Plunger driver 50 comprises, in the shown embodiment, two internal longitudinal ribs 51. These longitudinal ribs 51 interact with longitudinal grooves 61 on the outer surface of a plunger rod 60. Thus, the plunger rod 60 is rotationally locked to plunger driver 50 but may axially slide along these ribs 51.

Plunger driver 50 further comprises a longitudinal slit 55 though its wall. With this longitudinal slit 55, the plunger driver 50 is connected to the inner end of the first spring 40. Thus, a force applied to the plunger driver 50 by the first spring 40 is transmitted to the plunger rod 60 due to the engagement of internal longitudinal ribs 51 into longitudinal grooves 61.

On the other hand, the plunger driver 50 comprises at least one external longitudinal rib 52. In the embodiment shown, four such ribs are provided spaced at 90° to each other. The external longitudinal ribs 52 are slidably received in longitudinal grooves 74 of the plunger drive locking means 70. Thus, as long as the plunger drive locking means 70 is prevented from being rotated due to the locking engagement with the container driver 32, the plunger driver 50 and the plunger rod 60 are prevented from being rotated although the force of the first spring 40 acts on the plunger driver 50. However, once the plunger drive locking means 70 is free to rotate, the plunger driver 50 and the plunger rod 60 also start to rotate, caused by the first spring 40. In the initial stage of the injection device 1, i.e. prior to its use, a proximal part of the plunger rod 60 is received in the central opening of the container driver 32. As shown in FIG. 6, the central opening of container driver 32 comprises a threaded structure 38 that engages with the threads 63 of the plunger rod 60. Thus, the threaded proximal section of the plunger rod 60 is screw threaded in the interior of the container driver 32. Due to this threaded engagement, rotation of the plunger rod upon use of the injection device results in an axial displacement of the plunger rod towards the proximal end of the injection device. In other words, the plunger rod 60 is rotated by the thread engagement in the direction of the medicament container 12, and causes the stopper (not shown) in the medicament container holder 12 and in abutment with spinner 65 to move towards the proximal end of the medicament container holder in order to expel medicament. The torque force of spring 40 will continue to drive the plunger rod towards the proximal end of the injection device 1 pressing the stopper to expel medicament through the needle 13. The container driver 32 slides over along the plunger rod 60 as the plunger rod continues to move towards the proximal end of the device. The injection is completed when the stopper is at the proximal end of the medicament container.

When the plunger rod 60 is fully rotated towards the proximal end of injection device 1, the two legs of the U-bracket 81 are no longer supported by the longitudinal grooves of the plunger rod 60. Thus, the radial legs 86 at the proximal ends of the U-bracket can disengage the slits in the plunger driver 50. The spiral spring (not shown) coaxially arranged with the indicator rod 82 causes indicator assembly to move distally until the indicator 80 contacts the distal front surface of the distal housing part 3. This causes the distal protrusion of the indicator 80 to project through the indicator opening 83 provided in the centre of the distal wall of the distal housing part 3. This provides a visible and tactile indication to the user that the complete dose has been expelled.

Figure 7:
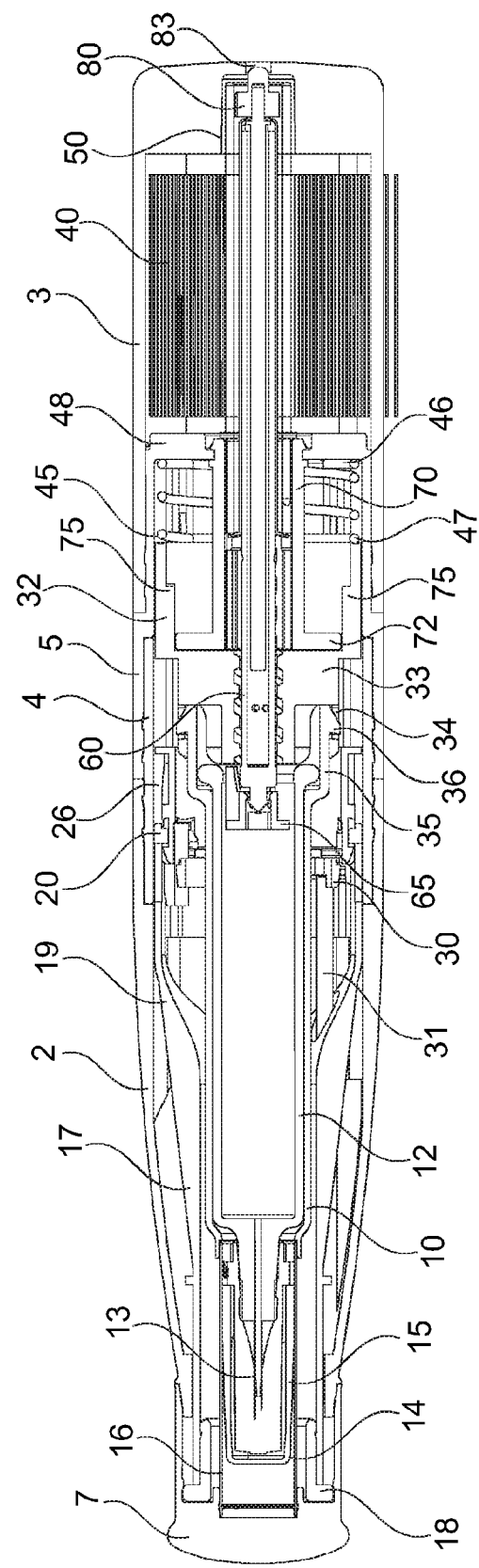
FIG. 7 shows a sectional view of the injection device according to the preferred embodiment of the invention in the initial position.

FIG. 7 shows a sectional view of the injection device 1 according to the preferred embodiment of the present invention in the initial position. In particular, FIG. 7 shows how the second spring 45 is located in the interior of the distal intermediate housing part 5. The distal end 46 of the second spring 45 is in contact with the inner surface of the distal radial wall of the distal intermediate housing part 5. Alternatively, it may be in contact with a ledge provided at the inside of the distal intermediate housing part, proximal to the distal radial wall of the distal intermediate housing part 5. The proximal end 47 of the second spring 45, on the other hand, abuts against a distal surface of the container driver 32.

Figure 8:
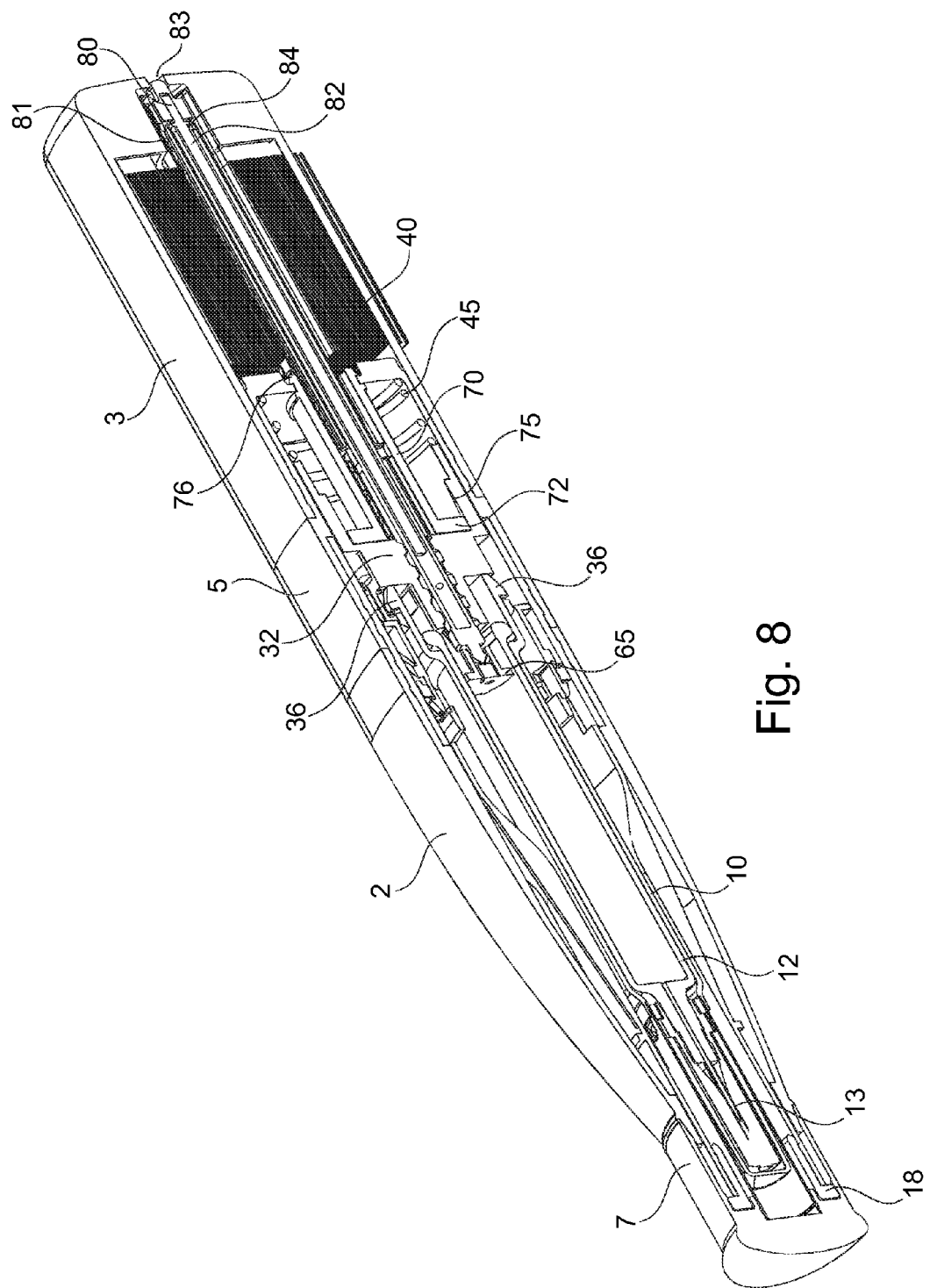
FIG. 8 shows a perspective view of the injection device according to the preferred embodiment of the invention in the initial position as shown in FIG. 7.

The same cross-sectional view is shown in FIG. 8, however as a perspective view in order to provide a different view of the various components relative to each other and their interengagement. Furthermore, in FIG. 8 the relative arrangement of the indicator 80, U-bracket 81, indicator rod 82, and injector distal opening 83 can be seen. The indicator rod 82 substantially extends within a central bore of the plunger rod 60. At the distal end of the injection device 1, a distal part of the injector rod 82 extends beyond the distal end of the plunger rod 60, and is received in an inner central bore of the indicator 80. The indicator rod 82 comprises a circumferential flange 84 adjacent to its distal end. Seen in axial direction, between the circumferential flange 84 and the proximal surface of the indicator 80, the intermediate part of the U-bracket 81 is located. As seen in FIG. 5, this intermediate part of U-bracket 81 comprises a throughhole through which the distal part of the indicator rod 82 extends. The two legs of the U-shaped bracket 81 extend in axial direction towards the proximal end of the plunger rod 60. At its proximal ends, the two legs of the U-bracket 81 each comprise a radial leg 86. This radial legs 86 project into corresponding radial openings in the plunger driver 50 (see FIG. 5).

Figure 9:
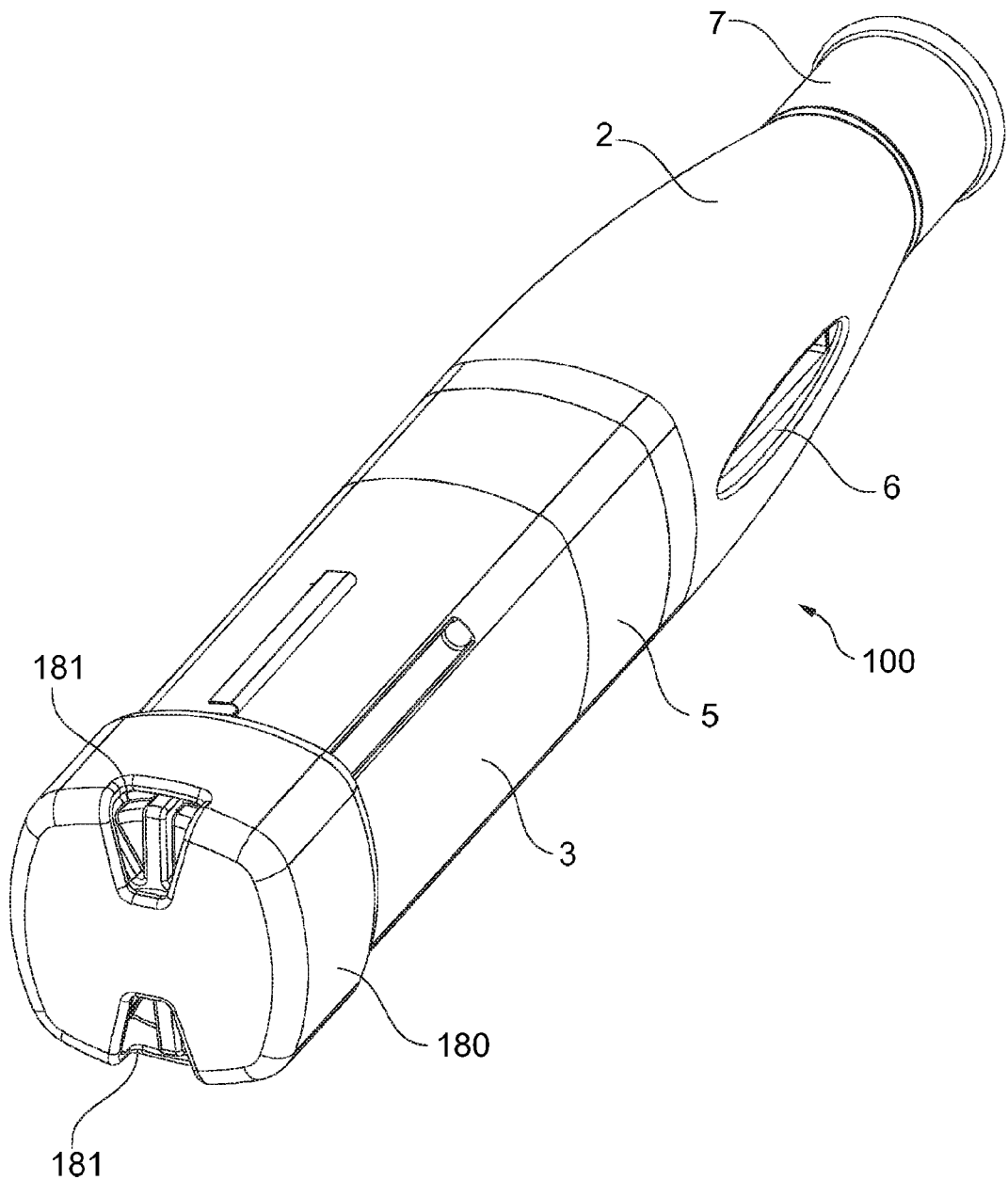
FIG. 9 shows a perspective view of a second preferred embodiment of the invention.

FIG. 9 shows a perspective view of a second preferred embodiment of the present invention. The injection device 100 shown in FIG. 9 is to a large extent identical to the injection device 1 according to the first preferred embodiment of the present invention. Same components are labelled with identical reference numerals. In the following, only the differences between the first and the second preferred embodiment will be explained in detail.

As shown in FIG. 9, the injection device 100 is different from the injection device 1 with respect to the indicator assembly that is provided to show end of dose. The structure for needle penetration and medicament injection shown in FIGS. 2 through 6 is also present in the injection device 100 of FIGS. 9 to 12.

Figure 10:
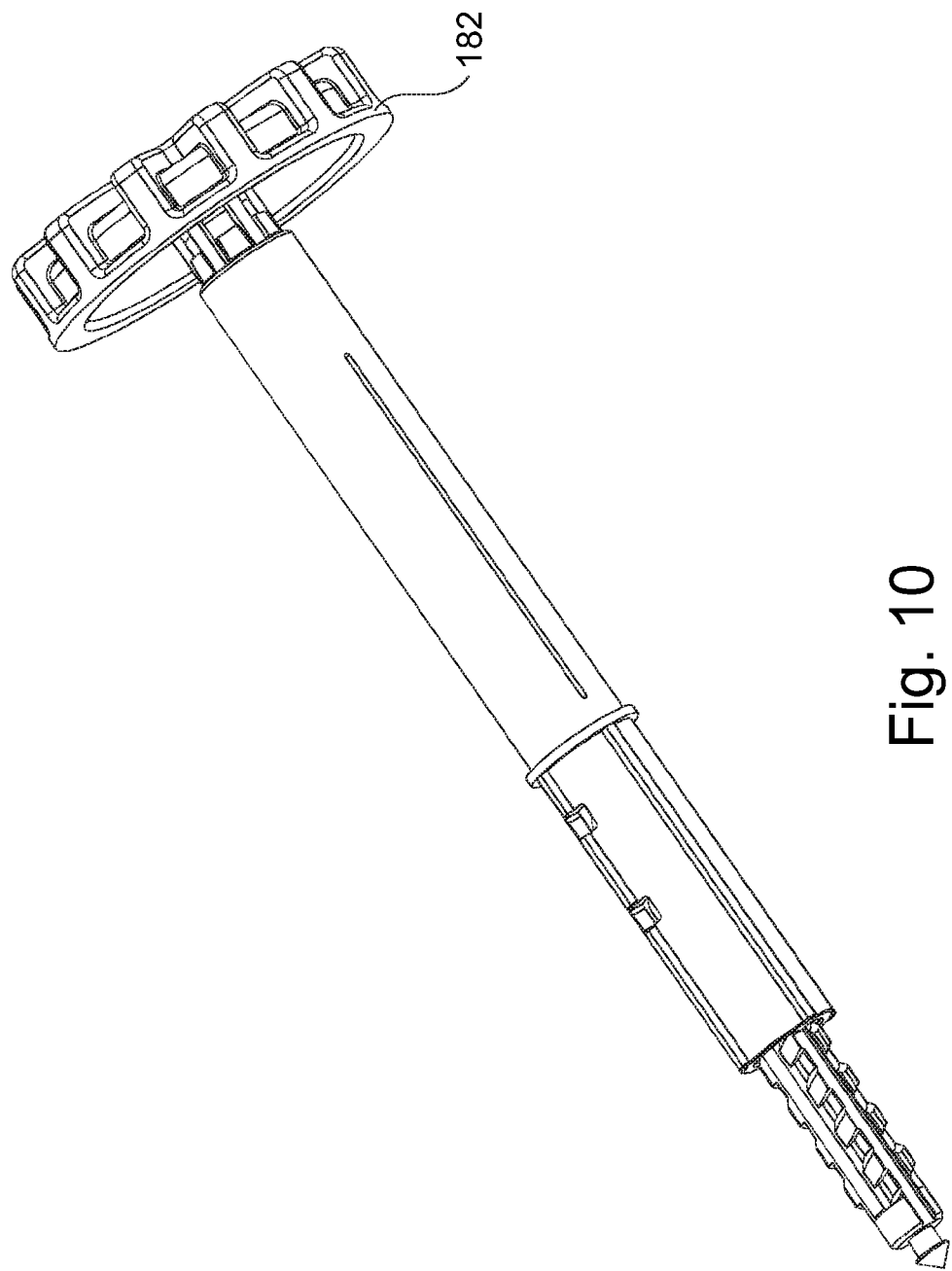
FIG. 10 shows a perspective view of details of the second preferred embodiment.

The second preferred embodiment shown in FIG. 9 comprises an indicator assembly 180 provided at the distal end of the housing. The indicator assembly comprises a cap having at least one opening 181. In the embodiment shown in the drawings, two opposing openings/windows 181 are provided. Through these openings 181, the user can see a signalling element in the form of a rotatable wheel or disk 182, which is also shown in FIG. 10. The window is preferably placed in the transition between a side surface and a distal end surface of the cap.

Figure 11:
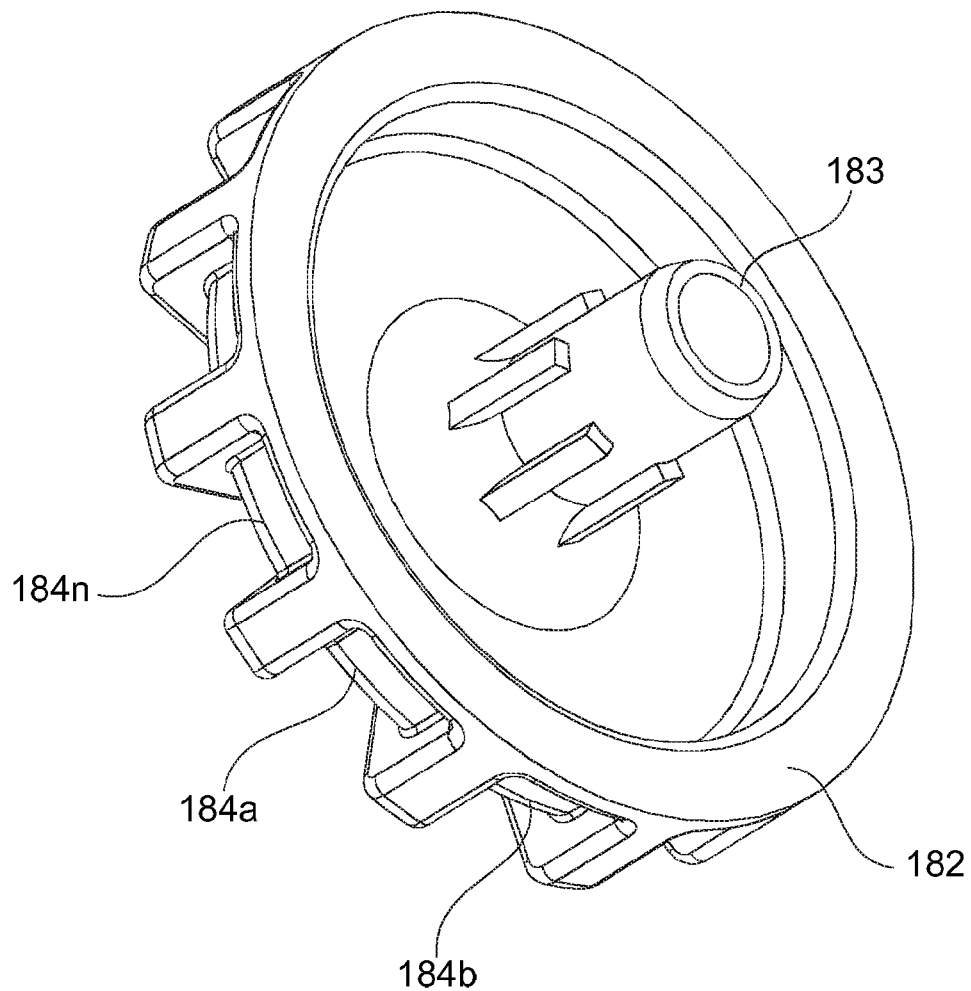
FIG. 11 shows a perspective view of details of the second preferred embodiment

As shown in FIG. 11, the rotatable disk 182 comprises a cylindrical proximal protrusion 183, such as a wheel hub. By means of this wheel hub 183, the rotatable disk 182 is connected to the distal end of the plunger driver 50. Thus, upon rotation of the plunger driver 50 by the first spring 40, also the rotatable disk 182 rotates. This can be seen by the user through the windows 181. Thus, the user can readily see that the device works properly and that an injection is in progress.

Figure 12:
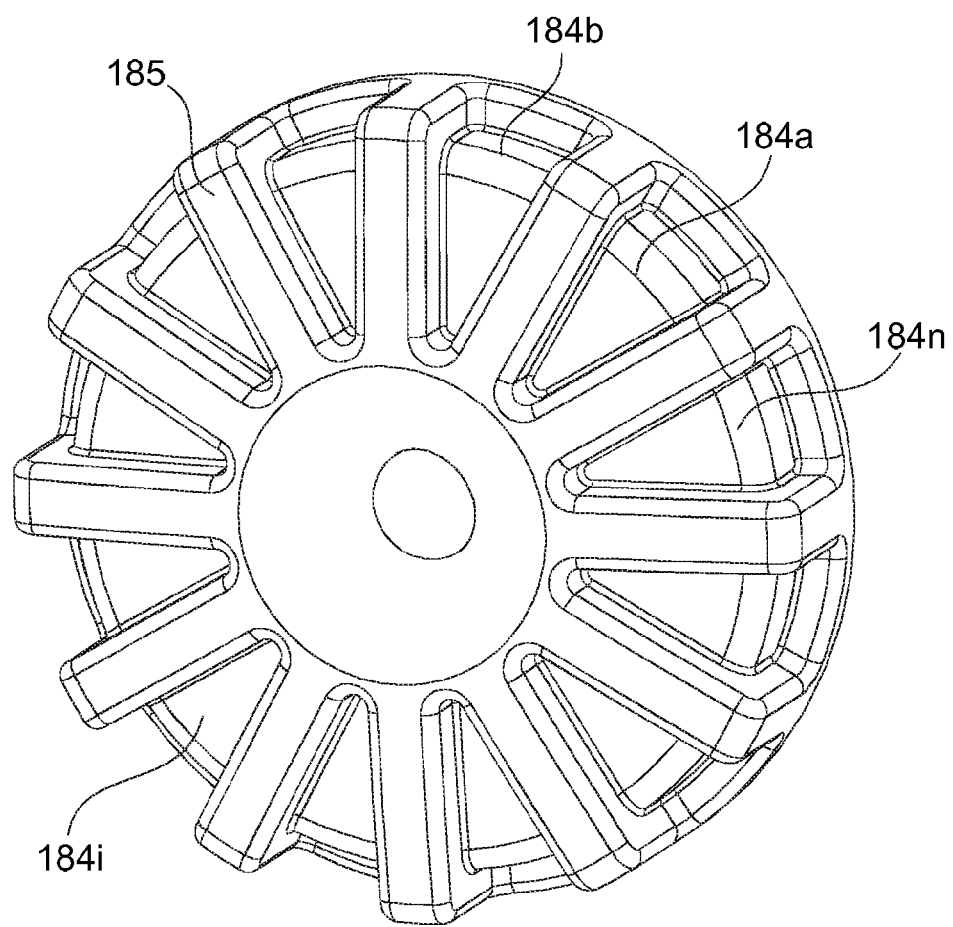
FIG. 12 shows a perspective view of details of the second preferred embodiment.

As also shown in FIG. 11 and FIG. 12, the rotatable disc comprises a distal indication structure having a plurality of segments 184a, . . . , 184i, . . . , 184n. These segments 184 alternate with radial ribs 185. When the rotatable disk 182 rotates, the alternating structure of ribs and segments passes windows 181. In a preferred embodiment, the segments 184 and/or the ribs 185 comprise indication elements. For example, the segment 184 or rib 185 shown in the window in the initial stage of the injection device 100 contains a first indication element, whereas the segment 184 or rib 185 shown in the window in the final position of the injection probably comprises a second, different indication element so that the user can easily distinguish the initial stage prior to injection from the final stage after injection of the medicament. For example, the segments 184 are coloured in different colours. Alternatively (not shown in the drawings), the angular widths of the segments may vary, for example from a very small width to a wide width in order to distinguish the initial position from the final position.

Figure 13:
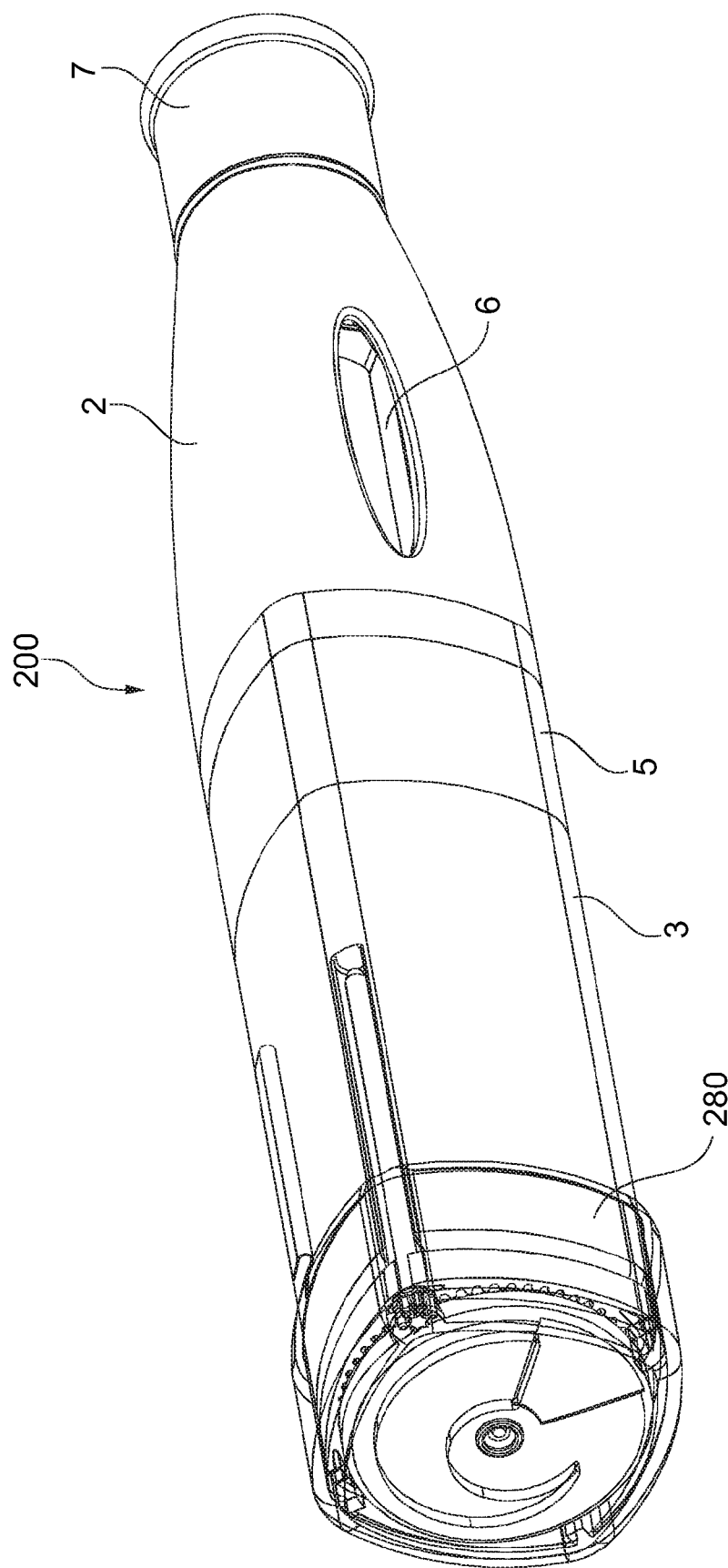
FIG. 13 shows a perspective view of a third preferred embodiment of the invention.

FIG. 13 shows a third preferred embodiment according to the present invention. The injection device 200 shown in FIG. 13 is identical to injection devices 10 and 100 according to the first and second preferred embodiments, except for the indicator assembly provided at the distal end of the injection device 200. Thus, the structure for needle penetration and medicament injection shown in FIGS. 2 through 6 is also present in the injection device 200 of FIGS. 13 and 14.

Figure 14:
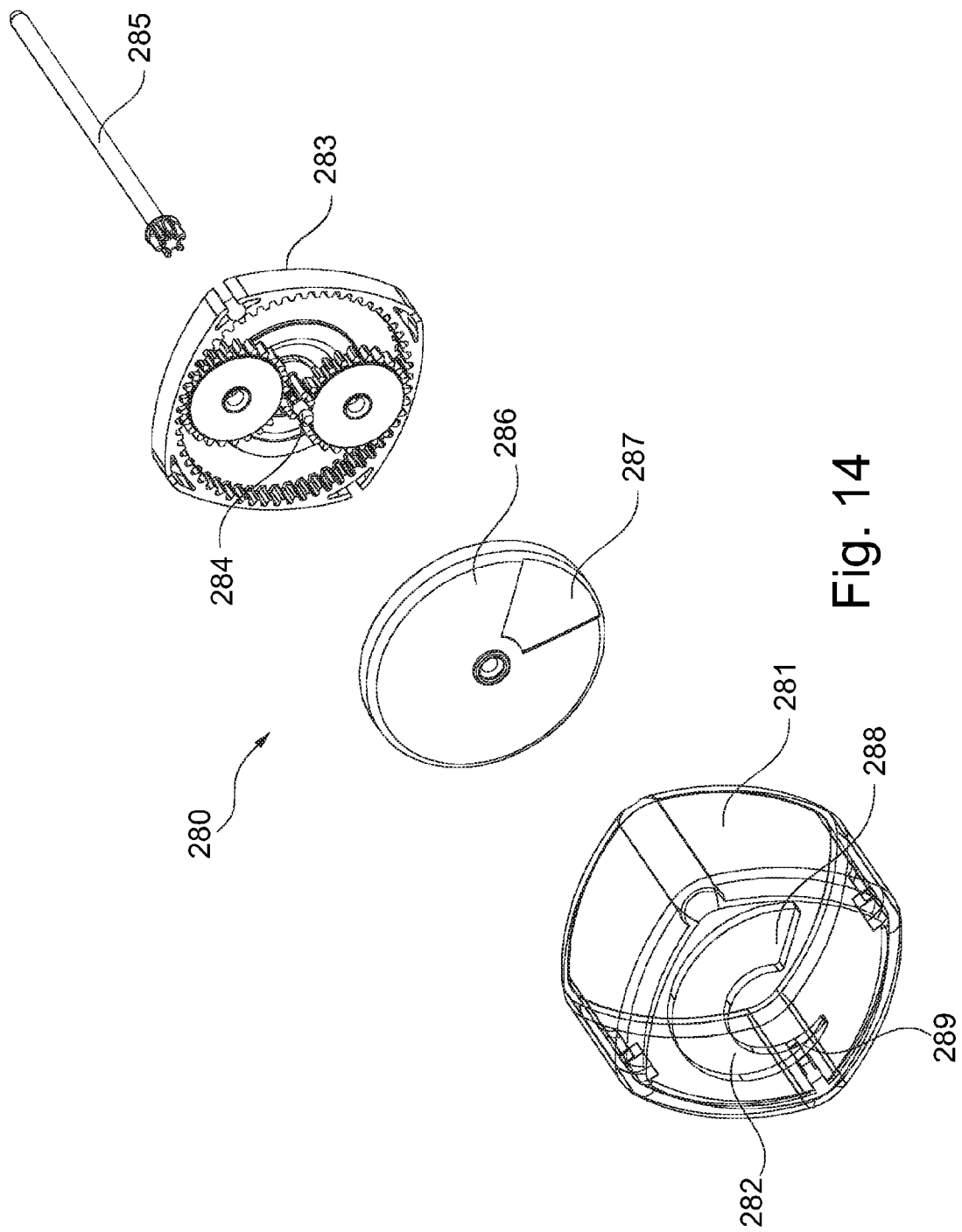
FIG. 14 shows an exploded view of the indication assembly of the third preferred embodiment.

Injection device 200 comprises an indicator assembly 280. FIG. 14 shows an exploded view of the indicator assembly 280. The indicator assembly 280 comprises a distal indicator assembly cap 281 which is mounted to the proximal housing part 3, for example by means of a press or snap fit. At the distal surface being perpendicular to the longitudinal axis of the injection device 200, an opening or window 282 is provided.

Within the indicator cap 281, a planetary gear assembly 283 is located. The solar wheel 284 of the planetary gear is connected to the plunger driver 50 at the distal end thereof.

Furthermore, an indicator disc 286 is located axially between the planetary gear assembly 283 and the distal wall of the indicator cap 281. The indicator disc 286 comprises an indicator area 287. The indicator area 287 is distinguishable from the remaining area of the indicator disk 286, for example by means of a different colour or a different texture. In the initial position of the injection device 200, the indicator assembly 280 is arranged such that the indicator area 287 is located at one side of the window 282. In general terms, the window may have any kind of crescent-shaped form. Alternatively, it may have the form of an L. In case of a crescent-shaped form, at one end of the window the side faces of the window may contact each other (such as side 289), whereas the other end may be truncated (such as side 288). Thus, the indicator assembly 280 may arranged such that the indicator area 287 is located at the side of the window having the largest width (side 288). Thus, the user can see a large part of the indicator element through the window 282. During injection of the medicament, the indicator disc 286 rotates, and concurrently, the indicator element 287 is rotated towards the other end of window 282, i.e. towards small end 289. Thus, the area of the indicator element 287 seen by the user is decreased, which visualizes to the user the progress of the injection, and also indicates to the user end of dose.

FIG. 14 also shows indicator pin 285 which is also in engagement with the planetary gear assembly 283. Such pin 285 may be optionally provided to have an additional signalling element at the outer surface of the distal housing part 5, as seen in FIG. 13.

The second and third preferred embodiments comprise a rotary injection indication mechanism 180, 280 for indicating to the user the progress of the injection. These rotary injection indication mechanisms 180, 280 comprise a signalling element and a drive mechanism for rotationally driving said signalling member. The drive mechanisms are coupled to the plunger driver 50 at the distal end thereof. Furthermore, these rotary injection indication mechanisms are arranged such that the progress of injection is shown through at least one opening provided at least in a distal end surface of the housing.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. An injection device, comprising:
   a housing;
   a container holder arranged within the housing and configured for accommodating a medicament container having a needle attached to one end of the medicament container and a stopper sealingly and slidably arranged inside the medicament container at the other end of the medicament container;
   a plunger rod arranged with a proximal end thereof configured to contact the stopper;
   first and second energy accumulating members arranged in an interior of the housing and configured to accumulate and store energy;
   a plunger drive mechanism slidably arranged in relation to the plunger rod, rotationally locked to the plunger rod, and rotatable in relation to the housing, the plunger drive mechanism being operationally associated with the first energy accumulating member; and a container driver configured to connect to the container holder and threadedly connected to the plunger rod, the container driver being operationally associated with the second energy accumulating member such that, due to an output axial force from the second energy accumulating member, the container holder and the plunger rod are axially movable in relation to the housing a predetermined distance toward a proximal end of the injection device from an initial locked position to a second position, whereby a needle penetration is performed;

wherein, in the initial locked position, the plunger drive mechanism is rotationally locked by the container driver, and the plunger drive mechanism is releasable such that, due to an output torque from the first energy accumulating member, the plunger drive mechanism is rotated and the plunger rod is urged toward the proximal end, whereby an injection is performed.

2. The injection device of claim 1, further comprising a container driver locking mechanism rotatable in relation to the housing and to the container driver, and configured to hold the container driver in the initial locked position and to release the container driver from the initial locked position toward the proximal end to the second position.

3. The injection device of claim 2, wherein the first energy accumulating member comprises a first end connected to the plunger drive mechanism and a second end connected to the housing.

4. The injection device of claim 3, wherein the first energy accumulating member includes a constant force spring.

5. The injection device of claim 1, wherein the second energy accumulating member is arranged between the container driver and a ledge on an inner surface of the housing.

6. The injection device of claim 1, further comprising a needle shield sleeve slidably arranged in a proximal part of the housing and configured to act on the container driver locking mechanism when the needle shield sleeve is pressed against an injection site.

7. The injection device of claim 6, wherein the needle shield sleeve and the container driver locking mechanism are operationally connected such that axial movement of the needle shield sleeve toward a distal end of the injection device causes the container driver locking mechanism to rotate.

8. The injection device of claim 7, wherein rotation of the container driver locking mechanism releases the container driver.

9. The injection device of claim 6, further comprising a resilient device that urges the needle shield sleeve toward the proximal end of the injection device when the injection device is removed from an injection site.

10. The injection device of claim 9, further comprising a locking mechanism for locking the needle shield sleeve against moving toward the distal end of the injection device when the injection device is removed from the injection site.

11. The injection device of claim 10, wherein the needle shield sleeve locking mechanism includes a container driver lock.

12. The injection device of claim 7, wherein the needle shield sleeve and the container driver locking mechanism are operationally connected by a cam-groove-mechanism.

13. The injection device of claim 1, further comprising an injection indication mechanism for indicating a progress of an injection.

14. The injection device of claim 13, wherein the injection indication mechanism includes an axial injection indication mechanism for indicating that the injection has come to an end.

15. The injection device of claim 14, wherein the axial injection indication mechanism includes a signaling element and an indication drive mechanism for axially driving the signaling member.

16. The injection device of claim 15, wherein the indication drive mechanism is coupled to the plunger drive mechanism.

17. The injection device of claim 15, wherein the axial injection indication mechanism is arranged such that a visible signal and a tactile signal signal the end of the injection.

18. The injection device of claim 15, wherein the signaling element includes a pin that moves distally from an initial position to a final position relative to the housing when the injection has come to the end.

19. The injection device of claim 18, wherein a distal end surface of the housing includes a through hole, and a distal end of the pin protrudes out of the through hole in the final position.

* * * * *